United States Patent [19]

Poli

[11] Patent Number: 4,673,681

[45] Date of Patent: Jun. 16, 1987

[54] PHARMACEUTICAL METHODS HAVING DOPAMINERGIC ACTIVITY

[75] Inventor: Stefano Poli, Milan, Italy

[73] Assignee: Poli Industria Chimica S.p.A., Milan, Italy

[21] Appl. No.: 847,395

[22] Filed: Apr. 2, 1986

[30] Foreign Application Priority Data

Apr. 4, 1985 [IT] Italy ............................... 20234 A/85

[51] Int. Cl.$^4$ ............................................. A61K 31/44
[52] U.S. Cl. .................................................... 514/288
[58] Field of Search ......................................... 514/288

[56] References Cited

PUBLICATIONS

A Rating Scale for Depression by: Max Hamilton.
The Evaluation of Extrapyramidal Disease by: Roger C. Duvoisin.
A Comparative, Multicenter Trial between Bromocriptine and Amitriptyline in the Treatment of Endigenous Depression.
The Lancet, vol. 1, p. 735, Apr. 8, 1978.
Physician's Desk Reference 1982, p. 1684-Sandoz-Cont.
Critical Analysis of the Disability in Parkinson's Disease by: David D. Webster, MD.
Chem. Abst. (1969)-71 42281p.

Primary Examiner—Stanley J. Friedman
Attorney, Agent, or Firm—Michael J. Striker

[57] ABSTRACT

A pharmaceutical composition containing α-dihydroergocryptine, or a salt thereof, is used in combination with pharmaceutically acceptable carrier means or excipient for the treatment of Parkinson's disease, depression or cephalalgias is disclosed. A method for administering the composition to a patient is also provided.

4 Claims, No Drawings

PHARMACEUTICAL METHODS HAVING DOPAMINERGIC ACTIVITY

The present invention concerns a new therapeutical use of α-dihydroergocryptine and pharmaceutical compositions containing the same as an active agent for the treatment of parkinsonism, depression and cephalalgias.

α-dihydroergocryptine or 12'-hydroxy-2'-(1-methylethyl)-5'α-(2-methylpropyl)-9,10-dihydro-ergotaman-3',6',18-trione, is a known compound, derived from the hydrogenation of the double bond, in position 9,10 of the natural alkaloid α-ergocryptine. This compound is generally used in association with dihydroergocristine and dihydroergocornine, for the therapy of cerebrovascular disturbances especially for elderly persons.

The capacity of dihydroergocryptine and, generally, of other similarly hydrogenated alkaloids, to bind α and D receptors at different levels in the CNS and peripherally is known. On the basis of such pharmacological activities, the primary use for which dihydroergocryptine, alone or in association, has been used up to now, is the senile cerebrovascular insufficiency in its many manifestations.

It has now been surprisingly discovered that dihydroergocryptine, event when active in the cited pathologies, can be advantageously used for the treatment of pathological conditions of the Central Nervous System such as parkinsonism, essential cephalalgias and depressions, the etiological causes of which can be linked to a dopaminergic lack. The treatments known, in fact, foresee the administration of 1-DOPA or ergolinic derivatives α-bromocriptine and ergotamine (Calne D. B., Lancet (1978) 1, 735 and Theohar C., Arzneim. Forsch. (1982) 32, 783). The latter treatments, however, besides the dopaminergic agonistic action, induce an undesired peripheral activity suggesting that it is preferable to avoid use of such treatments in a high percentage of patients due to the significant and severe side effects (for bromocriptine hypertension in 28% and syncope in 0.7% of cases; vomiting in 3% of cases; *Physicians' Desk Reference*, p. 1684 (36th ed. 1982).

Surprisingly, dihydroergocryptine, while being active in the treatment of the CNS pathology, as indicated above, did not show any of the side effects common to other ergolinic compounds already known.

This phenomenon leads to the finding that dihydroergocryptine has a selective dopaminergic activity for CNS which, prior to the present invention, was neither taught nor suggested by the prior art.

In the treatment of Parkinson's disease, dihydroergocryptine, administered as methanesulfonate, resulted in reducing tremors, akinesia and rigidity, at doseage levels of between 10 and 100 mg daily, when administered alone in de novo patients.

Typicals examples and results obtained in the treatment of Parkinson's disease are presented in Table 1. In Table 1, there are reported changes in symptomatology in seven de novo parkinsonian patients treated with dihydroergocryptine 40 mg/die:

TABLE 1

| De novo patients | BASAL VALUES | WEEKS OF TREATMENT | | | |
|---|---|---|---|---|---|
| | | 2 | 5 | 11 | 16 |
| WRS[1] | 14.86 ± 1.67 | 13.28* ± 1.91 | 12.14* ± 1.67 | 11.43* ± 1.68 | 10.43* ± 1.69 |
| CURS[2] | 30.14 ± | 28.86 ± | 26.71 ± | 23.57* ± | 21.71* ± |

TABLE 1-continued

| De novo patients | BASAL VALUES | WEEKS OF TREATMENT | | | |
|---|---|---|---|---|---|
| | | 2 | 5 | 11 | 16 |
| | 5.87 | 5.61 | 5.27 | 5.57 | 5.55 |

Legend to Table 1
[1]WRS: Webster Rating Scale (Webster, D. B., 1968 Modern Treatment, 5, 217);
[2]CURS: Columbia University Rating Scale (DUVOISIN R. C., 1970 - The evaluation of Extrapyramidal Disease. In "Monoamine, noyaux gris centraux et syndrome de Parkinson"; de Ajuriaggera J. (Ed.) Masson, Paris, pp. 313-325).
*P < 0.01 vs. basal values.

Moreover, dihydroergocryptine, administered in parkinsonian patients previously treated with 1-DOPA and bromocriptine, allowed the complete withdrawal of bromocriptine and the reduction of 1-DOPA dosage with an evident reduction of side effects, maintaining the same therapeutical activity level in the same patients.

In Table 2 there are reported, for example, the changes of symptomatology in seven parkinsonian patients, already treated with BCR+1-DOPA, after replacement of BCR with a placebo and subsequent introduction of dihydroergocryptine 40 mg/die:

TABLE 2

| Patients already under treatment with BRC + 1-DOPA | | | |
|---|---|---|---|
| | BRC | Placebo | Diidroergo-cryptine |
| WRS | 19.86* ± 1.84 | 22.71 ± 2.01 | 19.53* ± 2.23 |
| CURS | 30.57* ± 6.8 | 37.86 ± 6.97 | 30.0* ± 7.24 |

*P < 0.01 vs. placebo

Moreover, treatment with dihydroergocryptine was also discovered to be effective in the treatment of depression; a condition in which a dopaminergic lack is present. In the treatment of depressed patients, dihydroergocryptine showed a particularly good speed of effectiveness and a tolerability level higher than that of tricyclic antidepressants, thus leading to the conclusion that its elective use in elderly patients with depressive symptomatology would yield positive results.

Table 3 reports, for example, the evolution of depressive symptomatology in 18 patients treated with dihydroergocryptine drops 1.5–2 mg, three times daily.

TABLE 3

| HAMILTON RATING SCALE FOR DEPRESSION[1] | | | |
|---|---|---|---|
| Basal Values | After 7 Days | After 14 Days | After 21 Days |
| 34.61 ± 1.52 | 24.39* ± 1.93 | 17.44* ± 1.80 | 14.50* ± 1.72 |

[1]Hamilton M., 1960 - J. Neurol. Neurosurg. Psychiat., 23, 56
*P < 0.01 vs. basal values Chronically administered in patients with essential or vasomotor cephalalgias, dihydroergocryptine induced a 57.8% reduction in frequency and severity of headaches, allowing a recovery to an active, normal life and a lower consumption of antalgic agents.

α-dihydroergocryptine can be administered by oral, sublingual, parenteral or percutanous means as a pharmaceutical composition prepared for the foreseen use.

For the treatment of parkinsonism, daily dosage, expressed as methanesulfonate, can vary from 10 to 200 mg, according to weight and conditions of patients. Lower dosages are preferred, on the contrary, for the treatment of depression and cephalalgias, for example, from 2 to 20 mg in 1–3 administrations.

Pharmaceutical compositions, the object of the present invention, will be prepared according to conventional techniques, using compatible excipients and pharmaceutically acceptable carriers, and may contain, in combination, other active principles with complementary or, in any case, useful activity. Examples of these compositions prepared according to the present invention include capsules, pills, tablets, drops, ampoules for i.m. and i.v. administration, possible forms for prolonged administration of active principle (retard forms), etc.

The pharmaceutical compositions of the present invention will now be more fully described by the following examples of these types of preparations. It should, however, be noted that such examples are given by way of illustration and not of limitation.

Drops 100 ml contain:
Dihydroergocryptine methanesulfonate 200 mg
propylene glycol q.s.

Ampoules

Each ampoule contains:
Dihydroergocryptine methanesulfonate: 0.5 mg
propylene glycol: 100 mg
methanesolfinic acid q.s.: to pH=3
bidistilled water q.s.: to 1 ml Capsules One capsule contains:
Dihydroergocryptine methanesulfonate: 3 mg
starch, lactose, magnesium sterate, microcrystalline cellulose q.s.: to 100 mg While only several embodiments and examples of the present invention have been shown and described, it is obvious that many changes and modifications may be made thereunto, without departing from the spirit and scope of the invention.

What is claimed is:

1. A method for the treatment of a person with Parkinson's disease, cephalalgias or depression, comprising the step of:

administering an effective dosage of dihydroergocryptine, or a salt thereof, in combination with a pharmaceutically acceptable carrier means to said person.

2. The method according to claim 1, wherein said administering step includes the administration of from 10–100 mg/die of dihydroergocryptine mesylate as said effective dosage for the treatment of Parkinson's disease.

3. The method according to claim 1, wherein said administering step includes the administration of from 2–10 mg/die of dihydroergocryptine mesylate as said effective dosage for the treatment of depression.

4. The method according to claim 1, wherein said administering step includes the administration of from 2–10 mg/die of dihydroergocryptine mesylate as said effective dosage for the treatment of cephalalgias.

* * * * *